(12) United States Patent
Loescher

(10) Patent No.: US 6,596,913 B1
(45) Date of Patent: Jul. 22, 2003

(54) RECOVERY OF TERTIARY BUTYL ALCOHOL

(75) Inventor: Mitchell E. Loescher, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 09/977,610

(22) Filed: Oct. 15, 2001

Related U.S. Application Data
(60) Provisional application No. 60/271,240, filed on Feb. 23, 2001.

(51) Int. Cl.[7] .............................. C07C 2/08; C07C 2/14
(52) U.S. Cl. .................... 585/504; 585/510; 585/809; 585/868
(58) Field of Search ................ 585/504, 510, 585/804, 868

(56) References Cited

U.S. PATENT DOCUMENTS

| | | |
|---|---|---|
| 4,100,220 A | 7/1978 | Bowman et al. .... 260/683.15 R |
| 4,242,530 A | 12/1980 | Smith, Jr. .................. 585/510 |
| 4,375,576 A | 3/1983 | Smith, Jr. .................. 585/510 |
| 4,982,022 A | 1/1991 | Smith, Jr. et al. ........... 568/899 |
| 5,003,124 A | 3/1991 | Smith, Jr. et al. ........... 585/526 |
| 5,231,234 A | 7/1993 | Arganbright et al. ....... 568/697 |
| 5,336,841 A | 8/1994 | Adams ....................... 585/834 |
| 5,345,006 A | 9/1994 | Smith, Jr. .................. 568/899 |

Primary Examiner—Thuan D. Dang
(74) Attorney, Agent, or Firm—Kenneth H. Johnson

(57) ABSTRACT

A process for the dimerization of isobutene wherein tertiary butyl alcohol is used to enhance the selectivity of the catalyst to the dimer is disclosed wherein the tertiary butyl alcohol is removed from the diisobutene product by water wash. The water/TBA stream is then subjected to reextraction to remove the TBA for recycle to the dimerization reactor. The dimerization is preferably carried out in a reactor wherein the pressure is controlled to maintain the reaction mixture at is boiling point. Additional dimerization is carried out in a distillation column reactor that acts as a debutanizer to separate the unreacted isobutene form the product and the tertiary butyl alcohol.

8 Claims, 2 Drawing Sheets

RECOVERY OF TERTIARY BUTYL ALCOHOL

This application claim benefits of provisional application Ser. No. 60/271,290 filed Feb. 23, 2001.

BACKGROUND OF THE INVENTION

1. Field of the Invention

The present invention relates generally to a process for the production of diisobutene (DIB) wherein tertiary butyl alcohol (TBA) is used to modify an acid catalyst to provide more selectivity to the dimer. More particularly the invention relates to a process wherein the TBA and DIB are removed together as bottoms from a debutanizer column.

2. Related Art

One process for the dimerization of isobutene over an acid catalyst in the presence of tertiary butyl alcohol is disclosed in U.S. Pat. No. 4,100,220. The tertiary butyl alcohol is said to dehydrate the catalyst and provide for improved selectivity to the dimer.

Another liquid phase process for the oligomerization of $C_4$ and $C_5$ isoolefins is disclosed in U.S. Pat. No. 5,003,124 wherein the reaction mixture is allowed to boil to remove the heat of reaction and a further dimerization is obtained in a reactive distillation column. U.S. Pat. No. 4,242,124 discloses the reaction of isobutene with itself in a catalytic distillation column reactor to form diisobutene.

When tertiary butyl alcohol is used to improved the selectivity and separated from the unreacted $C_4$'s by fractional distillation, then all components boiling heavier than $C_4$ and lighter than DIB (referred to as heavies) may be removed along with the TBA and an azeotropic mixture of DIB. Since most feeds have at least some of these heavies, their build up must be prevented in the TBA recycle loop. A purge necessarily containing some TBA and DIB product is preferably withdrawn from the TBA loop. The purge represents a loss of isobutene (as TBA), a loss of feed heavies which might otherwise join the DIB in the gasoline pool, and some DIB product itself. Thus, the removal of the TBA from the DIB and heavies would be desirable.

SUMMARY OF THE INVENTION

Briefly the present invention comprises the removal of TBA from a first hydrocarbon stream into a water stream by contacting said streams under conditions of temperature and pressure to achieve extraction of said TBA into said water stream, and preferably the recovery of said TBA from said water stream by contacting said water steam containing said TBA with a second hydrocarbon stream under conditions of temperature and pressure to achieve extraction of said TBA into said second hydrocarbon stream. In a further preferred embodiment the TBA is a process enhancer in a process from which the first hydrocarbon stream originates and in a still further preferred embodiment the second hydrocarbon stream is a feed to the process from which the first hydrocarbon stream originates. Thus in a most preferred embodiment the TBA enhancer is removed from the product hydrocarbon stream of a process by contact with water into the water and then removed from the water by contact with the hydrocarbon feed into the hydrocarbon feed to the process from which the first hydrocarbon stream originated.

As used herein the term "TBA enhancer" means the TBA has a favorable effect on the process in question. The TBA may act as a homogeneous catalyst or catalyst modifier, although it may not be a reactant in the process. The TBA is present in very small amounts, usually in molar amounts of less than the reactant material, preferably a mol ratio of 0.001 to less than 1 mol of TBA/mol of reactants.

In a particular embodiment the present invention comprises the dimerization of isobutene over an acid catalyst in the presence of tertiary butyl alcohol (TBA). After the product diisobutene (DIB) and TBA has been separated from the unreacted $C_4$'s, the bottoms containing the TBA, DIB and heavies are washed with water in a liquid/liquid contact column to remove the TBA in the water phase. The DIB and heavies may then be sent to gasoline blending or for further processing. The TBA/water stream is then reextracted with a hydrocarbon stream, preferably $C_4$ feed, to remove and recycle the TBA.

The dimerization reaction may be effected in a standard single pass downflow fixed bed reactor, a distillation column reactor or combination as disclosed in U.S. Pat. No. 5,003,124 which is hereby incorporated by reference.

The term "reactive distillation" is used to describe the concurrent reaction and fractionation in a column. For the purposes of the present invention, the term "catalytic distillation" includes reactive distillation and any other process of concurrent reaction and fractional distillation in a column, i.e., a distillation column reactor, regardless of the designation applied thereto.

The catalyst beds as used in the present invention may be described as fixed, meaning positioned in a fixed area of the column and include expanded beds and ebulating beds of catalysts. The catalysts in the beds may all be the same or different so long as they carry out the functions of dimerization and hydrogenation as described. Catalysts prepared as distillation structures are particularly useful in the present invention.

DETAILED DESCRIPTION OF THE INVENTION

Figure 1:
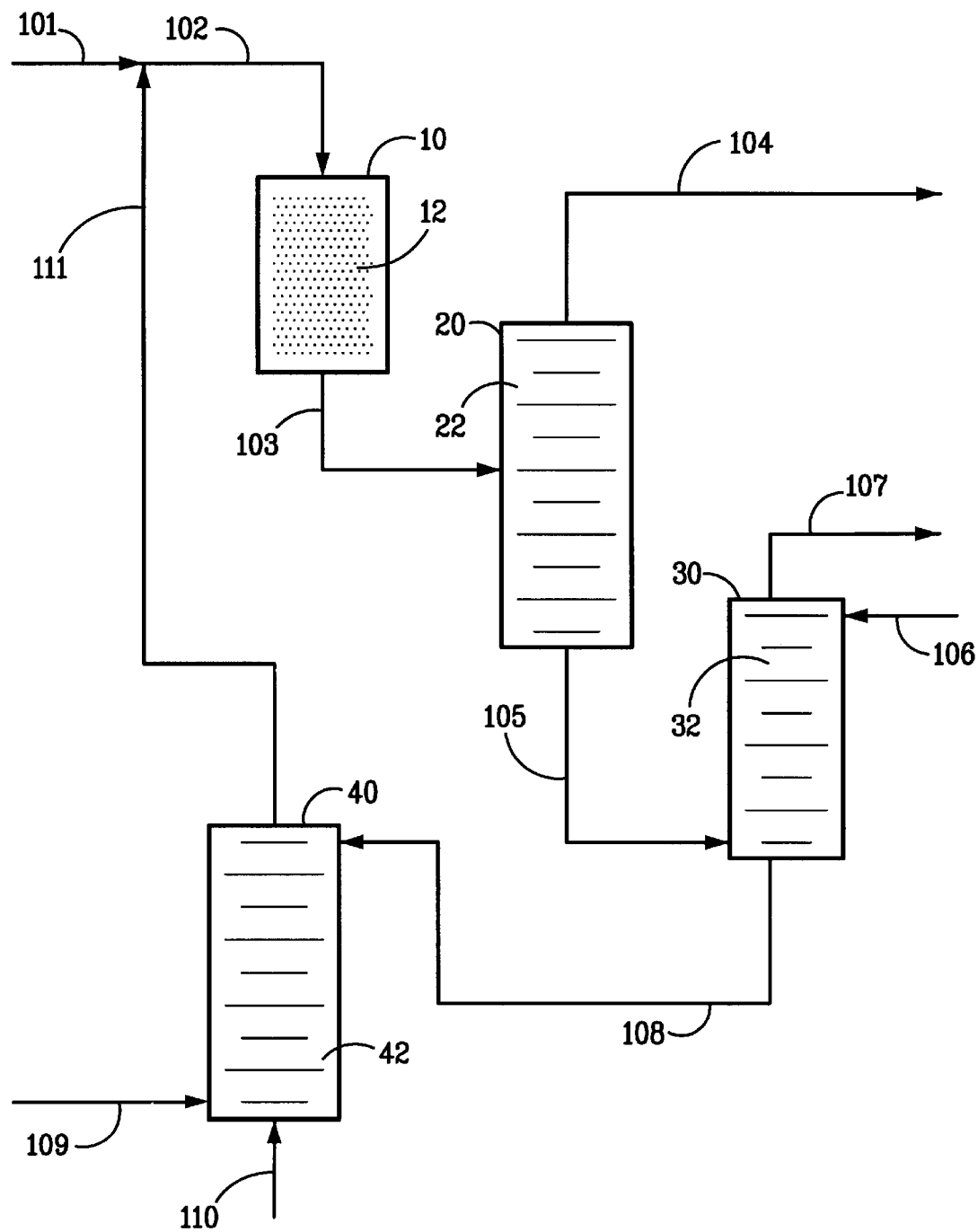
FIG. 1 is a flow diagram in schematic form of one embodiment of the invention.

Isobutene is dimerized to diisobutene according to the following reaction:

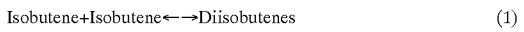

$$\text{Isobutene} + \text{Isobutene} \leftarrow\rightarrow \text{Diisobutenes} \qquad (1)$$

The dimerization of isobutene with itself is of particular interest because either of the isomers of diisobutene produce 2,2,4-trimethyl pentane (isooctane) when hydrogenated. If a catalytic distillation reactor is used the catalytic material employed in the process is preferably in a form to serve as distillation packing. Broadly stated, the catalytic material is preferably a component of a distillation system functioning as both a catalyst and distillation packing, i.e., a packing for a distillation column having both a distillation function and a catalytic function. The catalyst is prepared in the form of a catalytic distillation structure.

The dimerization catalyst may include either an acidic cation exchange resin or zeolite, which are generally employed as fine powders. Structures for this use are described in U.S. Pat. Nos. 4,215,011; 4,302,356; 4,443,559; 5,266,546 and 5,348,710 which are incorporated herein. Other catalytic distillation structures useful for this purpose are disclosed in U.S. Pat. Nos. 4,731,229; 5,073,236; 5,431,890 and 5,730,843 which are also incorporated by reference.

The mole sieve or cation exchange resin catalyst packing is of such a nature as to allow vapor flow through the bed, yet provide a sufficient surface area for catalytic contact as described in the previously noted patents. The catalyst packing is preferably arranged in the upper portion of the distillation column reactor, more preferably occupying about one-third to one half of the column. A rectification section may be located above the catalyst zone.

To provide the desired degree of temperature and residence time control, a process and apparatus are provided wherein the reaction liquid is boiling within a distillation column reactor. Overheads are withdrawn and condensed with some of the condensate being returned to the distillation column reactor as reflux. The advantage of the present process is that due to the continual reflux a portion of the selected dimer (diisobutene) is always condensing on the catalyst structure.

Several different arrangements have been disclosed to achieve the desired result. For example, British Patents 2,096,603 and 2,096,604 disclose placing the catalyst on conventional trays within a distillation column. A series of U.S. patents, including those listed above and more, particularly U.S. Pat. Nos. 4,443,559 and 4,215,011 disclose using the catalyst as part of the packing in a packed distillation column. The use of multiple beds in a reaction distillation tower is also known and illustrated, for example, in U.S. Pat. Nos. 4,950,834; 5,321,163; and 5,595,634.

The catalyst component may take several forms. In the case of particulate catalytic material, generally from 60 mm to about 1 mm down through powders, is enclosed in a porous container such as screen wire or polymeric mesh. The material used to make the container must be inert to the reactants and conditions in the reaction system. The screen wire may be aluminum, steel, stainless steel, and the like. The polymer mesh may be nylon, Teflon, or the like. The mesh or threads per inch of the material used to make the container is such that the catalyst is retained therein and will not pass through the openings in the material. Catalyst particles of about 0.15 mm size or powders may be used and particles up to about ¼ inch diameter may be employed in the containers.

In the present process the first hydrocarbon stream containing TBA may be contacted with the water stream in either concurrent or countercurrent flow. The contacting may be carried out at pressures ranging from subatmospheric to superatmospheric and at temperatures ranging from ambient to several hundred degrees C., preferably 50 to 200 psig and more preferably 75 to 125 psig at 20 to 40° C.

The contact of the TBA containing water stream may be contacted with the second hydrocarbon stream under the same range of conditions of pressure and temperature as the first contact which favor the removal of the TBA to the second hydrocarbon stream.

In addition to the conditions of temperature and pressure, the mass transfer effect of the extractions may be enhanced by having the extracting liquid (water or hydrocarbon) present in a volume excess to the extractant liquid (the liquid containing TBA, from which TBA is to be removed, either water or hydrocarbon), preferably from about 1 to 5 volumes of extracting liquid per volume of extractant liquid. Referring now to FIG. 1 a simplified flow diagram of one embodiment of the invention is shown. The feed containing the isobutene to be dimerized and TBA is fed via flow line 101 to a reactor 10 containing a bed of acidic cation exchange resin 12. The effluent from the reactor in flow line 103 is fed to a debutanizer 20 containing vapor/liquid contact structures 22 where the $C_4$ and lighter material is taken overheads via flow line 104. The material in flow line 104 may be recycled as feed if desired (not shown). The bottoms from the debutanizer containing product DIB, TBA and heavies (other hydrocarbon material boiling heavier than $C_4$) are taken via flow line 105 and fed to water wash column 30 containing liquid/liquid contact structures 32 where it is contacted with water fed near the top by flow line 106. The product DIB is taken as overheads from this column via flow line 107 and the liquid water phase containing the TBA is taken as bottoms via flow line 108. The bottoms in flow line 108 is fed to extraction column 40 containing liquid/liquid contact structure 42 where it is contacted with hydrocarbon feed containing the isobutene. The water is removed as bottoms via flow line 110 and may be recycled to column 30 (not shown). The hydrocarbon feed containing the isobutene and TBA is then recycled to the reactor via flow line 111 and 103. If desired all of the feed in line 101 may also be fed to the extraction column 40 where the feed will be water washed to remove contaminants. Generally all of the feed is water washed (not shown).

Figure 2:
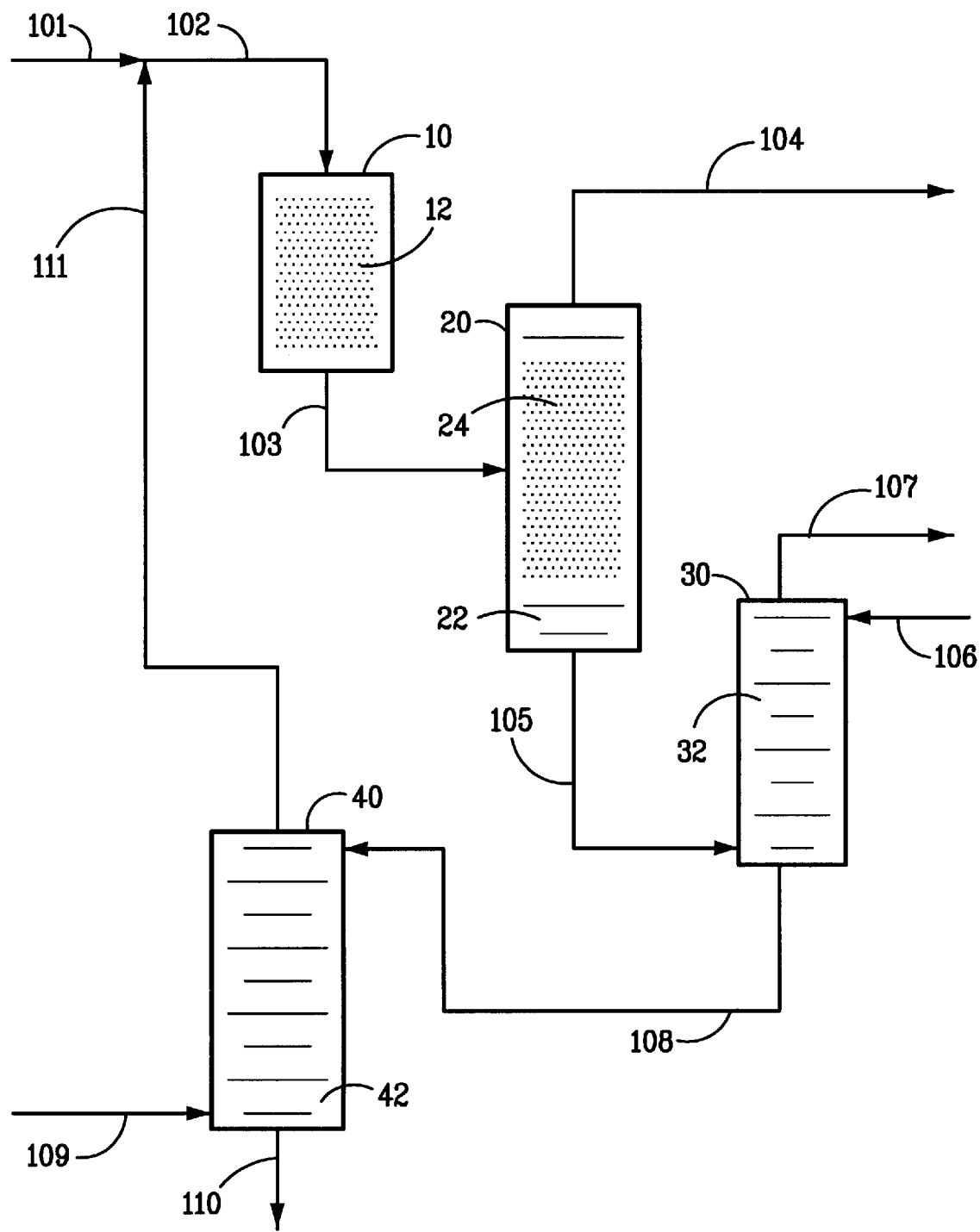
FIG. 2 is a flow diagram in schematic form of another embodiment of the invention.

Referring now to FIG. 2 a simplified flow diagram of a second embodiment is shown. All of the components are numbered the same as FIG. 1 for ease of reference. The only difference between the embodiments is that a bed 24 of acid ion exchange catalyst is placed within the debutanizer 20 where further reaction of isobutene with itself to form additional DIB occurs concurrently with the separation of unreacted isobutene and other $C_4$ and lighter components which are taken as overheads via flow line 104. The bottoms from the debutanizer containing product DIB, TBA and heavies (other hydrocarbon material boiling heavier than $C_4$) are taken via flow line 105 and fed to water wash column 30 containing liquid/liquid contact structures 32 where it is contacted with water fed near the top by flow line 106. The product DIB is taken as overheads from this column via flow line 107 and the liquid water phase containing the TBA is taken as bottoms via flow line 108. The bottoms in flow line 108 is fed to extraction column 40 containing liquid/liquid contact structure 42 where it is contacted with hydrocarbon feed containing the isobutene. The water is removed as bottoms via flow line 110 and may be recycled to column 30 (not shown). The hydrocarbon feed containing the isobutene and TBA is then recycled to the reactor via flow line 111 and 103. If desired all of the feed in line 101 may also be fed to the extraction column 40 where the feed will be water washed to remove contaminants. Generally all of the feed is water washed (not shown).

Preferably the reactor 10 is operated at a pressure such that the mixture is boiling at between 120 and 300° F. whereby a portion but less than all of the mixture is vaporized, said reaction occurring in the liquid phase. This allows the heat of reaction to be absorbed by the boiling liquid without any increase in reaction temperature.

The invention claimed is:

1. In a process for the dimerization of isobutene to diisobutene wherein tertiary butyl alcohol is included in the feed to the dimerization to improve the selectivity to dimer and the unreacted feed is separated from the product diisobutene and tertiary butyl alcohol, the improvement comprising removing the tertiary butyl alcohol from the diisobutene product by water washing to form a water wash product.

2. The process according to claim 1 further comprising the step of extracting the tertiary butyl alcohol from the water wash product with hydrocarbon and recycling the tertiary butyl alcohol to the process.

3. The process according to claim 2 wherein said hydrocarbon is the feed to the process.

4. A process for the dimerization of isobutene to form diisobutene comprising the steps of:
 (a) feeding a stream containing isobutene and tertiary butyl alcohol to a reactor containing an acidic catalyst;
 (b) reacting a portion of said isobutene with itself in said reactor to form diisobutene;
 (c) feeding the effluent from said reactor containing unreacted isobutene, diisobutene and tertiary butyl alcohol to a fractional distillation column wherein unreacted isobutene is separated from diisobutene and tertiary butyl alcohol;
 (d) removing unreacted isobutene from said fractional distillation column as overheads;
 (e) removing diisobutene and tertiary butyl alcohol from said fractional distillation column as bottoms;
 (f) washing said bottoms with water to remove the tertiary butyl alcohol in a water phase;
 (g) extracting the tertiary butyl alcohol from said water phase with a hydrocarbon to form a hydrocarbon containing said extracted tertiary butyl alcohol; and
 (h) recycling said tertiary butyl alcohol to said reactor.

5. The process according to claim 4 wherein the hydrocarbon of step (g) contains isobutene and said hydrocarbon containing said extracted tertiary butyl alcohol is fed to said reactor.

6. The process according to claim 4 wherein said reactor the pressure in said reactor is maintained such that the reaction mixture contained therein is at its boiling point such that the heat of reaction is absorbed by the boiling liquid in the reactor.

7. The process according to claim 4 wherein said fractional distillation column contains a bed of acidic catalyst such that additional isobutene is reacted with itself to form additional diisobutene concurrently with said separation.

8. A process for the dimerization of isobutene to form diisobutene comprising the steps of:
 (a) feeding a stream containing isobutene and tertiary butyl alcohol to a reactor containing an acidic catalyst;
 (b) reacting a portion of said isobutene with itself in said reactor to form diisobutene while maintaining the reactor pressure such that the mixture within said reactor is boiling in the range of 120 to 300° F. whereby a portion but less than all of the mixture is vaporized, said reaction occurring in the liquid phase;
 (c) feeding the effluent from said reactor containing unreacted isobutene, diisobutene and tertiary butyl alcohol to a fractional distillation column containing a bed of acidic catalyst wherein additional isobutene is reacted with itself to form diisobutene and unreacted isobutene is concurrently separated from diisobutene and tertiary butyl alcohol;
 (d) removing unreacted isobutene from said fractional distillation column as overheads;
 (e) removing diisobutene and tertiary butyl alcohol from said fractional distillation column as bottoms;
 (f) washing said bottoms with water to remove the tertiary butyl alcohol in a water phase;
 (g) extracting the tertiary butyl alcohol from said water phase with a hydrocarbon stream containing isobutene; and
 (h) recycling said extracted tertiary butyl alcohol to said reactor.

\* \* \* \* \*